United States Patent [19]

Cherkofsky et al.

[11] 4,064,260
[45] Dec. 20, 1977

[54] ANTI-INFLAMMATORY DIARYLIMIDAZOTHIAZOLES AND THEIR CORRESPONDING S-OXIDES

[75] Inventors: Saul Carl Cherkofsky; Thomas Ray Sharpe, both of Wilmington, Del.

[73] Assignee: E. I. Du Pont de Nemours and Company, Wilmington, Del.

[21] Appl. No.: 709,819

[22] Filed: July 29, 1976

[51] Int. Cl.$^2$ ............................................. C07D 513/04
[52] U.S. Cl. ................................... 424/270; 260/301; 260/306.7 T; 548/324
[58] Field of Search ...................... 260/306.7 T, 301; 424/270

[56] References Cited

U.S. PATENT DOCUMENTS

| | | | |
|---|---|---|---|
| 3,328,415 | 6/1967 | Surrey et al. | 260/301 |
| 3,455,924 | 7/1969 | Lednicer | 260/306.7 T |
| 3,720,683 | 3/1973 | Breuer et al. | 260/301 |
| 3,732,212 | 5/1973 | Carabateas | 260/301 |
| 3,932,395 | 1/1976 | Hideg et al. | 260/306.7 T |

*Primary Examiner*—R. J. Gallagher

[57] ABSTRACT

Diarylimidazothiazoles, such as 2,3-dihydro-5,6-bis(p-methoxyphenyl)imidazo[2,1-b]thiazole, useful as antiinflammatories.

21 Claims, No Drawings

ANTI-INFLAMMATORY DIARYLIMIDAZOTHIAZOLES AND THEIR CORRESPONDING S-OXIDES

BACKGROUND

This invention relates to anti-inflammatory imidazothiazole derivatives.

Iwai et al., in U.S. Pat. No. 3,267,112, disclose anti-inflammatory imidazothiazoles, such as 6-methyl-imidazo[2,1-b]thiazole.

Pyl et al., in *Ann.* 643, 145–153 (1961) disclose the preparation of 5,6-diphenylimidazo[2,1-b]thiazole and its 2-methyl and 2,3-dimethyl derivatives.

Mazur et al., in *Khim-Farm, Zh.,* 3 (8), 11–15 (1969) disclose the preparation of 2,3-dihydro-5,6-diphenylimidazo [2,1-b]thiazole as a potential anthelmintic agent.

Mohan et al., in *Indian J. Chem.,* 11(8) 747-9 (1973), disclose the preparation of 2,3-dihydro-5,6-diphenyl-4H-imidazo[2,1-b]thiazole.

Lednicer, in U.S. Pat. No. 3,455,924, discloses anti-inflammatory dianisylimidazoles, including those of the following formula:

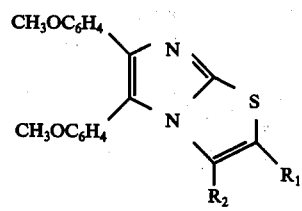

where $R_1$ and $R_2$ can be hydrogen, alkyl, alkoxy, hydroxy, or nitro.

There is a continuing need for safe and effective anti-inflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and anti-inflammatory drugs are often used in their treatment. The usefulness of most commercial anti-inflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new anti-arthritic compounds with minimal side effects.

SUMMARY

According to this invention there is provided compounds of the following formula, pharmaceutical compositions containing them, and methods of using them for treatment of arthritis.

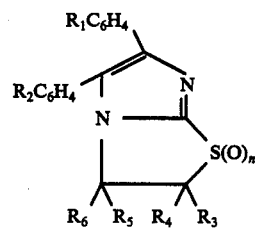

where $n = 0$, 1, or 2;

$R_1$ and $R_2$, alike or different, $= C_1-C_4$ alkoxy;

$R_3$, $R_4$ and $R_6 = $ H or F; and $R_5 = $ H.

DETAILED DESCRIPTION

Synthesis

These compounds are synthesized from anisoin in two or three steps as shown in the following scheme.

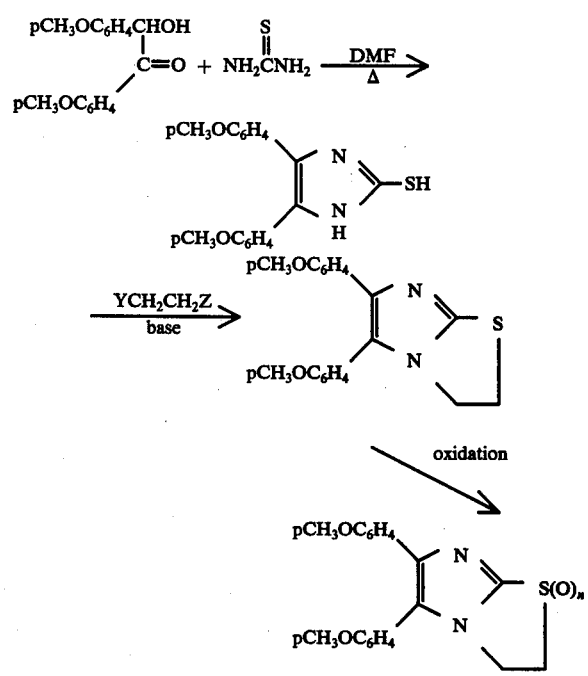

In the cyclization reaction to give the sulfide, Y and Z are the same or different, and can be halogen (Cl, Br, I), p-toluenesulfonate, or other leaving groups. Bases (and solvents) that can be used are potassium carbonate (DMF) alkali metal alkoxides (alcohols) and amines (chloroform). In the oxidation to sulfoxides and sulfones ($n = 1$ or 2) m-chloroperoxybenzoic acid can be used in methylene chloride or chloroform (at temperatures from 0° to reflux). Other peracids as well as other oxidizing agents can be used in the oxidation step.

Compounds where $R_3$, $R_4$, and $R_6$ are fluorine, are made as shown in the following scheme:

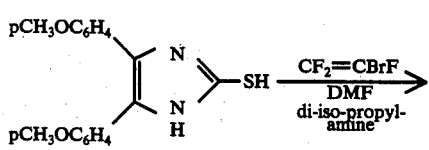

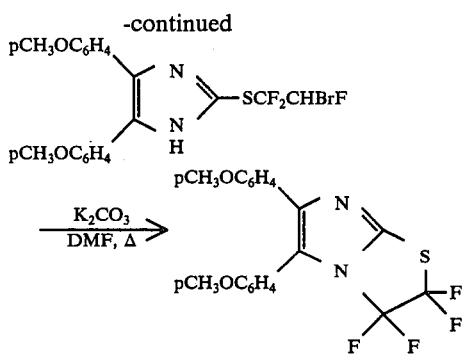

Other bases (such as sodium alkoxide in alcohol) can be used for the cyclization.

The following examples further illustrate the processes for making these compounds.

EXAMPLE 1

2,3-Dihydro-5,6-bis(p-methoxyphenyl)imidazo[2,1-b]thiazole

To a stirred slurry of 3.1 g (0.01 mole) 4,5 bis-(p-methoxyphenyl)-2-mercaptoimidazole [Anschutz and Schwickerath, Ann., 284, 24 (1895)] in 50 ml methanol was added 0.65 g (0.012 mole) of sodium methoxide. To the resulting solution was added 2.6 g (0.011 mole) 2-chloroethyl-p-toluenesulfonate in 10 ml methanol. The mixture was heated at reflux overnight. Another 0.5 g (0.002 mole) of 2-chloroethyl-p-toluenesulfonate was added and refluxing was continued another 2 hours. The mixture was poured into ice water and extracted with methylene chloride three times. The methylene chloride layers were dried and concentrated on a rotary evaporator. The residue was chromatographed on silica gel, eluting with chloroform. The product was obtained by trituration of fractions 4 and 5 with ether to give crystalline material, m.p. 149°–151°. Analysis by IR, NMR and CHN microanalysis indicated the product in a purity of about 85%.

Preparation of this compound by a similar procedure, followed by recrystallization from ethanol, then from n-chlorobutane, resulted in pure product, m.p. 156°–7°. IR: 3.39, 3.45, 3.54μ (saturated CH); 6.17, 6.32, 6.42, 6.57, 6.68μ (aromatic C═C and/or C═N); 8.02μ (C—O—C); 11.97μ (para disubstituted aromatic). NMR: 3.7, 3.8δ (2 singlets, 6H); 3.6–4.2δ (mult, 4H); 6.6–7.5δ (2 overlapping $A_2B_2$ quartets, 8H). Mass spectrum: Calcd for $C_{19}H_{18}N_2O_2S$ 338.1088; Found 338.1087.

Anal. Calcd $C_{19}H_{18}N_2O_2S$: C, 67.43; H, 5.36; N, 8.28. Found: C, 67.38; H, 5.55; N, 8.09.

EXAMPLE 2

2,3-Dihydro-5,6-bis(p-methoxyphenyl)imidazo[2,1-b]thiazole

A mixture of 46.8 g (0.15 mole) of 4,5-bis(p-methoxyphenyl)-2-mercaptoimidazole, 55.5 g (0.15 mole) of ethylene glycol di-p-toluenesulfonate [Helv. Chim Acta 29 1675 (1946); Chem Abs. 41 1641 g] and 45.5 g (0.33 mole) potassium carbonate in 500 ml dimethylformamide was stirred at room temperature for 3 days. The mixture was poured into ice water and the precipitated product was collected and washed with water. Recrystallization from 1200 ml ethanol gave 31.3 g (61%) of product, m.p. 155°–8°.

EXAMPLE 3

2,3-Dihydro-5,6-bis(p-methoxyphenyl)imidazo[2,1-b]thiazole S-oxide and S,S-dioxide To a solution of 30.4 g (0.09 mole) of 2,3-dihydro-5,6-bis(p-methoxyphenyl)imidazo[2,1-b]thiazole in 300 ml methylene chloride was added dropwise a solution of 40 g (0.2 mole) of ~85% pure m-chloroperoxybenzoic acid in 500 ml methylene chloride. Another 4 g of peracid was added in two portions over the next 4 hours. The mixture was then stirred at room temperature for 2 days. The mixture was washed four times with 300 ml of 10% sodium bicarbonate solution. The methylene chloride layer was dried and concentrated on a rotary evaporator. The residue was chromatographed on silica gel (650g), eluting with chloroform to give after recrystallization from toluene, 9.1 g (27%) of the S,S-dioxide. Further elution with ethyl acetate gave, after recrystallization from ethanol, 2.9 g (9%) of the S-oxide.

The S,S-dioxide was characterized as follows: m.p. 238.5°–240.5°; IR: 3.32, 3.38, 3.53μ (saturated CH); 6.17, 6.32, 6.44, 6.55, 6.70μ (aromatic C═C and/or C═N); 7.55 and 8.81μ ($SO_2$); 8.00μ (aryl—O—C); broad 11.95μ (para disubstituted aromatic). NMR: 3.8, 3.9δ (2 singlets, 6H); 4.0–4.6δ (mult, 4H); 6.7–7.6δ (2 overlapping $A_2 B_2$ quartets, 8H).

Anal. Calcd for $C_{19}H_{18}N_2O_4S$: C, 61.61; H, 4.90; N, 7.56. Found C, 61.67; H, 4.95, N, 7.37.

The S-oxide was characterized as follows: m.p. 194°–6°; IR: 3.34, 3.42 and 3.53μ (saturated CH); 6.22, 6.37, 6.47, 6.58, 6.73μ (aromatic C═C and/or C═N); 8.02μ (aryl—O—C); 9.52μ (S→O); 11.95μ (para disubstituted aromatic). NMR: 3.75, 3.85δ (2 singlets, 6H); ~3.6–4.6δ (mult, 4H); 6.7–7.6δ (2 overlapping $A_2B_2$ quartets, 8H).

Anal Calcd $C_{19}H_{18}N_2O_3S$: C, 64.39; H, 5.12; N, 7.90. Found: C, 64,87; H, 5.14; N, 8.17; C, 63.88; H, 5.11; N, 8.35; C, 64.11; H, 5.18; N, 7.96.

EXAMPLE 4

2,3-Dihydro-2,2,3-trifluoro-5,6-bis(p-methoxyphenyl)imidazo-[2,1-b]thiazole

A mixture of 0.95 g (2 mmoles) of 2-(2-bromo-1,1,2-trifluoroethylthio)-4,5-bis(p-methoxyphenyl) imidazole, 0.6 g (4 mmoles) potassium carbonate and 10 ml dimethylformamide was stirred at 50°–60° for 2 days. The mixture was poured into ice water. The aqueous mixture was extracted three times with ether. The ether was backwashed three times with water, then dried and concentrated on a rotary evaporator. The residue, 0.5 g of crystals, was combined with 0.3 g of product with precipitated from the aqueous layers on standing. The combined crude product was recrystallized from methyl cyclohexane to give 0.7 g of pure product, m.p. 160°–2°. IR: 3.32μ, ═CH; 3.50μ, sat. CH; 6.15, 6.54, 6.61μ, C═C and C═N; strong 8.02μ, aryl C—O; 9.67μ, C—F.H—NMR: 3.8, 3.85δ (2 singlets, 6H); two doublets 5.6, 6.4δ ($J_{HF_1}$ ~61 cps; $J_{HF_1}$ ~7 cps; $J_{HF_3}$ ~0–1 cps, 1H); 2 overlapping $A_2B_2$ quartets 6.7–7.6δ (8H). F—NMR: $F_2$: two doublets, 75.09 and 72.82δ; $F_3$: two doublets, 86.88 and 89.16δ; $F_1$: two doublets centered at 139.78δ ($J_{HF_1}$ ~61 cps; $J_{HF_2}$ ~7 cps; $J_{HF_3}$ ~1 cps; $J_{F_1F_2}$ ~4 cps; $J_{F_1F_3}$ ~8.5 cps; $J_{F_2F_3}$ ~213 cps).

Anal. Calcd. Calcd. $C_{19}H_{15}F_3N_2O_2S$: C, 58.16; H, 3.85 N, 7.14. Found: C, 58,31; H, 4.10; N, 7.08.

Dosage Forms

The anti-arthritic agents of this invention can be administered to alleviate inflammation and pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 50 milligrams per kilogram of body weight. Ordinarily 0.1 to 20, and preferably 0.1 to 10 milligrams per kilogram per day given in divided doses two to four times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5 – 95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble pharmaceutically acceptable acid salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Use

A standard procedure for detecting and comparing the anti-inflammatory activity of compounds in this series for which there is good correlation with human efficacy is the adjuvant-induced arthritis test in rats.

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Myobacterium butyricum* suspended in mineral oil 5 mg./ml.). 20 Non-arthritic controls are injected with mineral oil. The animals are held for 2 weeks to allow development of arthritis. Paw volumes (uninjected, left hand paw) are measured and the adjuvant injected rats are culled and distributed to treatment groups of 10 of equal disease severity. Non-arthritic controls are distributed to 2 groups of 10. The rats are given oral doses of compound or PVA-Acacia (10 ml./kg.) on that day and on the 6 following days. One day after the last dose the paw volumes (uninjected, left hind paw) are measured using a Ugo Basile Volume Differential Meter Model 7101.

$$\frac{\text{Arthritic Control Mean Paw Volume (ml.)} - \text{Treatment Group Mean Paw Volume (ml.)}}{\text{Arthritic Control Mean Paw Volume (ml.)} - \text{Non-arthritic Control Mean Paw Volume (ml.)}} \times$$

100% = % Decrease From Control Mean Paw Volume.

Dose-response regression lines of the % decrease are plotted on semi-log paper by visual fit and the ED50% decrease from control paw volume is determined by inspection.

An equally reliable test that is used for testing analgesic activity of compounds is the phenylquinone writhing test in mice.

Writhing was caused in mice by the intraperitoneal injection of phenyl-p-benzoquinone (Siegmund, E., Cadmus, R., Lu, G., *Proc. Soc. Exp. Biol. and Med.*, 95, 729, 1957).

Groups of 10 or more Carworth CF-lS male mice, 18-21 g each, were fasted 17-21 hours and were intubated with the writhing antagonist at several dose levels in 0.5% methylcellulose. 30 Minutes later the mice were challenged with phenylquinone (1.25 mg./kg., i.p., dissolved in ethanol and diluted to 5% ethanol with distilled water at 40° C.). At 30–40 minutes after the antagonist, the mice were observed for appearance of the writhing syndrome. The number of mice which did not writhe at all during the 10 minute observation period was recorded as a quantal index of analgesia. $ED_{50}$'s were obtained by the Litchfield and Wilcoxon Method (Litchfield, J. T. and Wilcoxon, F., *J.P.E.T.*, 96, 99 1949) and the Weil moving average method (Weil, C., *Biometrics*, 8, 249 1952). Peak time studies were also done with some of these compounds and their peak time $ED_{50}$'s were recorded.

When tested by these procedures, the following $ED_{50}$ dosages were determined.

BIOLOGICAL DATA

| COMPOUND | | | | | Rat Adjuvant Arthritis | Mouse phenylquinone writhing (analgesic) |
|---|---|---|---|---|---|---|
| n | $R_3$ | $R_4$ | $R_5$ | $R_6$ | $ED_{50}$ (mg/Kg) | $ED_{50}$ (mg/Kg) |
| 0 | H | H | H | H | 5.5 | 64 |
| 1 | H | H | H | H | 7.4 | 8.7 |
| 2 | H | H | H | H | 8.0 | >130 |
| 0 | F | F | H | F | 11 | |

We claim:

1. A compound of the formula:

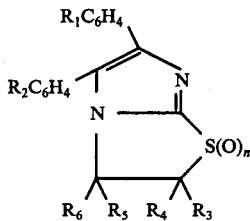

where
$n = 0$, 1, or 2;
$R_1$ and $R_2$, alike or different, $= C_1-C_4$ alkoxy;
$R_3$, $R_4$ and $R_6 =$ H or F; and $R_5 =$ H.

2. The compound of claim 1 where $R_1$ and $R_2$ are p-methoxy.

3. The compound of claim 2 where $R_3$, $R_4$, $R_5$, and $R_6$ are hydrogen.

4. The compound of claim 3 where $n=0$.

5. The compound of claim 3 where $n=1$.

6. The compound of claim 2 where $n=2$.

7. The compound of claim 2 where $n=0$, $R_3=F$, $R_4=F$, $R_5=H$, and $R_6=F$.

8. An anti-inflammatory composition consisting essentially of a pharmaceutically suitable carrier and an effective anti-inflammatory amount of a compound of claim 1.

9. An anti-inflammatory composition consisting essentially of a pharmaceutically suitable carrier and an effective anti-inflammatory amount of a compound of claim 2.

10. An anti-inflammatory composition consisting essentially of a pharmaceutically suitable carrier and an effective anti-inflammatory amount of a compound of claim 3.

11. An anti-inflammatory composition consisting essentially of a pharmaceutically suitable carrier and an effective anti-inflammatory amount of a compound of claim 4.

12. An anti-inflammatory composition consisting essentially of a pharmaceutically suitable carrier and an effective anti-inflammatory amount of a compound of claim 5.

13. An anti-inflammatory composition consisting essentially of a pharmaceutically suitable carrier and an effective anti-inflammatory amount of a compound of claim 6.

14. An anti-inflammatory composition consisting essentially of a pharmaceutically suitable carrier and an effective anti-inflammatory amount of a compound of claim 7.

15. A method of alleviating inflammation in a mammal which comprises administering to the mammal an effective anti-inflammatory amount of a compound of claim 1.

16. A method of alleviating inflammation in a mammal which comprises administering to the mammal an effective anti-inflammatory amount of a compound of claim 2.

17. A method of alleviating inflammation in a mammal which comprises administering to the mammal an effective anti-inflammatory amount of a compound of claim 3.

18. A method of alleviating inflammation in a mammal which comprises administering to the mammal an effective anti-inflammatory amount of a compound of claim 4.

19. A method of alleviating inflammation in a mammal which comprises administering to the mammal an effective anti-inflammatory amount of a compound of claim 5.

20. A method of alleviating inflammation in a mammal which comprises administering to the mammal an effective anti-inflammatory amount of a compound of claim 6.

21. A method of alleviating inflammation in a mammal which comprises administering to the mammal an effective anti-inflammatory amount of a compound of claim 7.

* * * * *